United States Patent
Underwood (10) Patent No.: US 11,234,985 B2
(45) Date of Patent: Feb. 1, 2022

(54) ANTIVIRAL THERAPY

(71) Applicant: VIIV HEALTHCARE COMPANY, Wilmington, DE (US)

(72) Inventor: Mark Richard Underwood, Research Triangle Park, NC (US)

(73) Assignee: Viiv Healthcare Company

( * ) Notice: Subject to any disclaimer, the term of this patent is extended or adjusted under 35 U.S.C. 154(b) by 0 days.

(21) Appl. No.: 16/835,733

(22) Filed: Mar. 31, 2020

(65) Prior Publication Data

US 2020/0230147 A1 Jul. 23, 2020

Related U.S. Application Data

(63) Continuation of application No. 15/838,738, filed on Dec. 12, 2017, now abandoned, which is a continuation of application No. 15/366,566, filed on Dec. 1, 2016, now abandoned, which is a continuation of application No. 15/073,728, filed on Mar. 18, (Continued)

(51) Int. Cl.
| | |
|---|---|
| A61K 31/535 | (2006.01) |
| A61K 31/505 | (2006.01) |
| A61K 31/5365 | (2006.01) |
| A61K 31/675 | (2006.01) |
| A61K 45/06 | (2006.01) |
| A61K 31/513 | (2006.01) |
| A61K 9/00 | (2006.01) |
| A61K 31/4985 | (2006.01) |
| A61K 31/52 | (2006.01) |
| A61K 31/536 | (2006.01) |

(52) U.S. Cl.
CPC ........ *A61K 31/5365* (2013.01); *A61K 9/0014* (2013.01); *A61K 9/0019* (2013.01); *A61K 9/0053* (2013.01); *A61K 31/4985* (2013.01); *A61K 31/505* (2013.01); *A61K 31/513* (2013.01); *A61K 31/52* (2013.01); *A61K 31/536* (2013.01); *A61K 31/675* (2013.01); *A61K 45/06* (2013.01)

(58) Field of Classification Search
CPC .......................... A61K 31/5365; A61K 31/513
USPC .............................................. 514/230.2, 274
See application file for complete search history.

(56) References Cited

U.S. PATENT DOCUMENTS

| | | |
|---|---|---|
| 5,034,394 A | 7/1991 | Daluge |
| 5,519,021 A | 5/1996 | Young et al. |
| | (Continued) | |

FOREIGN PATENT DOCUMENTS

| | | |
|---|---|---|
| EP | 0349242 | 1/1990 |
| EP | 0582455 | 2/1994 |
| | (Continued) | |

OTHER PUBLICATIONS

Selleseth, et al., Interactions of 1263W94 with Other Antiviral Agents in Inhibition of Human Cytomegalovirus Replication, Antimicrobial Agents and Chemotherapy (20030 47(4): 1468-1471.
(Continued)

*Primary Examiner* — Shengjun Wang
(74) *Attorney, Agent, or Firm* — Robert J. Smith (57) ABSTRACT

The present invention relates to combinations of compounds comprising HIV integrase inhibitors and other therapeutic agents. Such combinations are useful in the inhibition of HIV replication, the prevention and/or treatment of infection by HIV, and in the treatment of AIDS and/or ARC.

16 Claims, 2 Drawing Sheets

Related U.S. Application Data 2016, now abandoned, which is a continuation of application No. 14/710,952, filed on May 13, 2015, now abandoned, which is a continuation of application No. 13/575,380, filed as application No. PCT/US2011/022219 on Jan. 24, 2011, now abandoned.

(60) Provisional application No. 61/298,589, filed on Jan. 27, 2010.

(56) References Cited

U.S. PATENT DOCUMENTS

| | | | |
|---|---|---|---|
| 5,914,332 | A | 6/1999 | Sham et al. |
| 6,544,961 | B1 | 4/2003 | St. Clair et al. |
| 7,511,037 | B2 | 3/2009 | Naidu et al. |
| 8,088,770 | B2 | 1/2012 | Desai et al. |
| 8,129,385 | B2 | 3/2012 | Johns et al. |
| 8,624,023 | B2 | 1/2014 | Yoshida |
| 9,242,986 | B2 | 1/2016 | Kawasuji et al. |
| 10,426,780 | B2 | 10/2019 | Underwood |
| 2005/0171127 | A1 | 8/2005 | Currie et al. |
| 2006/0084627 | A1 | 4/2006 | Mardh |
| 2006/0246130 | A1 | 11/2006 | Dahl et al. |
| 2007/0124152 | A1 | 5/2007 | Johns et al. |
| 2008/0039428 | A1 | 2/2008 | Allaway et al. |
| 2008/0076738 | A1 | 3/2008 | Cai et al. |
| 2008/0207620 | A1 | 8/2008 | Desai et al. |
| 2008/0241289 | A1 | 10/2008 | Gant et al. |
| 2009/0075939 | A1 | 3/2009 | He et al. |
| 2009/0093454 | A1 | 4/2009 | Gudmundsson et al. |
| 2009/0181902 | A1 | 7/2009 | Desai et al. |
| 2009/0318421 | A1 | 12/2009 | Johns et al. |
| 2011/0076276 | A1 | 3/2011 | Guo et al. |

FOREIGN PATENT DOCUMENTS

| | | |
|---|---|---|
| EP | 1874117 | 2/2006 |
| JP | 2008540343 A | 11/2008 |
| JP | 4295353 | 4/2009 |
| WO | 91/17159 | 11/1991 |
| WO | 95/33464 | 12/1995 |
| WO | 96/30025 | 10/1996 |
| WO | 97/21685 | 6/1997 |
| WO | 99/48371 | 9/1999 |
| WO | 9955372 A1 | 11/1999 |
| WO | 2005112930 | 12/2005 |
| WO | 2006/096444 | 9/2006 |
| WO | 2006/116764 | 11/2006 |
| WO | 2007/079260 | 7/2007 |
| WO | 2007082922 | 7/2007 |
| WO | 2008/011117 | 1/2008 |
| WO | 2008/042240 | 4/2008 |
| WO | 2008/103949 | 8/2008 |
| WO | 20081103899 | 8/2008 |
| WO | 2009/005674 | 1/2009 |
| WO | 2009/005693 | 1/2009 |
| WO | 2009/007441 | 1/2009 |
| WO | 2009/008989 | 1/2009 |
| WO | 2009/058923 | 5/2009 |
| WO | 2009/059243 | 5/2009 |
| WO | 2009/082810 | 7/2009 |
| WO | 2009/082818 | 7/2009 |
| WO | 2009/082819 | 7/2009 |
| WO | 2009/088719 | 7/2009 |
| WO | 2009/100532 | 8/2009 |
| WO | 2009/148600 | 12/2009 |
| WO | 2010/011812 | 1/2010 |
| WO | 2010/068253 | 6/2010 |
| WO | 2011/094150 | 8/2011 |
| WO | 2011/128623 | 10/2011 |
| WO | 2011/160024 | 12/2011 |

OTHER PUBLICATIONS

Wenning, et al., Lack of Significant Drug Interaction between Raltegravir and Tenofovir, Antimicrobial Agents and Chemotherapy (2008) 52(9): 3253-3258.

Arribas, et al., Once-daily S/GSK1349572 as part of combination therapy in antiretroviral naïve adults: rapid and potent antiviral responses in the interim 16-week analysis from Spring-1 (ING112276), XVIII International Aids conference, Jul. 18-23, 2010, Vienna, Austria, Abstract, www.aids2010.org (http://pag.aids2010.org/Abstracts. aspx?AID=17600.

Brown, et al., Drug Interactions with New and Investigational Antiretrovirals, Clinical Pharmacokinetics (2009) 48(4):211-241.

Chesney, Adherence to HAART Regimens, (2003) AIDS Patient Care and STDS, 17(4):169-177.

Damond, et al., Virological and immunological response to HAART regimen containing integrase inhibitor in HIV-2 -infected patients, (2008) AIDS 22(5): 663-668, pp. 665-666.

De Clercq, Anti-HIV drugs: 25 compounds approved within 25 years after the discovery of HV, International Journal of Antimicrobial Agents, (2009) 33:307-320.

De Clercq, Perspectives of non-nucleoside reverse transcriptase inhibitors (NNRTIs) in the therapy of HIV-1 infection, (1999) II Farmaco 54:26-45.

Drug Data Report (2010) 32(9):893-895.

EPZICOM® Prescribing Information.

EPZICOM® Package Insert.

Eron, et al., Dolutegravir treatment response by baseline viral load and NRTI backbone in treatment-naïve HIV-infected individuals, Poster Abstract—P204, Journal of the Int'l AIDS Society (2012) 15(Suppl 4):18264.

Frank, Ian, Once-Daily HAART: Toward a New Treatment Paradigm, (2002) JAIDS J Acquired Immune Deficiency Syndromes, 31:S10-S15.

Fulco, et al., Reltegravir-Based HAART Regimen in a Patient with Large B-Cell Lymphoma, (2010) Annals Pharmacother 44:377-382 2010 (Published Online Dec. 29, 2009, theannals.com, DOI 10.1345/aph, 1M370).

Garrido, et al., New therapeutic strategies for raltegravir, J Antimicrob Chemother (2010) 65:218-223.

Gazzard, B.G., on behalf of the BHIVA Treatment Guidelines Writing Group, British HIV Association guidelines for the treatment of HIV-1-infected adults with antiretroviral therapy (2008) HIV Medicine 9:563-608.

GSK/Shionogi Clinical Trial, A Dose Ranging Trial of GSK1349572 and 2 NRTI in HIV-1 Infected, Therapy Valve Subjects (ING112276), ClinicalTrials.gov, Aug. 20, 2009, from the web archive Sep. 4, 2009: (http://web.archive.org/web/20090904062433/http://clinicaltrials.gov/ct2/show/NCT00951015).

GSK/Shionogi Clinical Trial, A Phase IIb Pilot Study to Assess the Antiviral Activity of GSK1349572 Containing Regimen in Antiretroviral Therapy (ART)-Experienced, HIV-1-infected Adult Subjects with Raltegravir Resistence, ClinicalTrials.gov archive, Jan. 15, 2010 (XP002743041), https://clinicaltrials.gov/archive/NCT00950859/2010_01_15.

Guidelines for the Use of Antiretroviral Agents in HIV-1-Infected Adults and Adolescents; Dec. 1, 2009, Developed by the DHHS Panel on Antiretroviral Guidelines for Adults and Adolescents—A Working Group of the Office of AIDS Research Advisory Council (OARAC), Nov. 3, 2008, pp. 1-161.

Hammer, et al., Antiretroviral Treatment of Adult HIV Infection—2008 Recommendations of the International AIDS Society—USA Panel, (2008) JAMA 300(5):555-570.

Harris, Marianne, New approaches to antiretroviral therapy—Looking back at a decade of progress, http://www.relaymagazine.com/meds-you/2008/new-approaches-to-antiretroviral-therapy.

Johns, et al., The Discovery of S/GSK1349572: A Once Daily Next Generation Integrase Inhibitor with a Superior Resistance Profile, Conference Reports for NATAP, 17th CROI, Conference on Retroviruses and Opportunistic Infections, San Francisco, CA, Feb. 16-19, 2010, 6 pages (http://www.natap.org/2010/CROI/croi_63.htm).

(56) References Cited

OTHER PUBLICATIONS

Kobayashi, et al., In Vitro Antiretroviral Properties of S/GSK1349572, a Next-Generation HIV Integrase Inhibitor, Antimicrobial Agents and Chemotherapy (2011) 55(2):813-821, published ahead of print on Nov. 29, 2010.

Lalezari, et al., Potent Antiviral Activity of S/GSK1349572, a Next-Generation Integrase Iinhibitor (INI), in INI-Naäve HIV-1-Infected Patients: ING111521 Protocol, IAS 2009, 5th IAS Conference on HIV Pathogenesis, Treatment and Prevention, Jul. 19-22, 2009, Capetown, South Africa—Abstract TUAB105, http://www.natap.org/2009/IAS/IAS 19.htm.

Lalezari, et al., Pharmacokinetics (PK) and Safety in Healthy Subjects of S/GSK1349572, a Next Generation, Once-Daily HIV Integrase Inhibitor (INI), 5th IAS Conference on HIV Pathogenesis, Treatment and Prevention, Jul. 19-22, 2009, Capetown, South Africa.

Lennox, et al., Safety and efficacy of raltegravir-based versus efavirenz-based combination therapy in treatment-naïve patients with HIV-1 infection: a multicentre, double-blind randomised controlled trial, (2009) Lancet 374:796-806.

Markowitz, et al., Rapid and Durable Antiretroviral Effect of the HIV-1 Ingegrase Inhibitor Raltegravir as Part of Combination Therapy in Treatment-Naïve Patients with HIV-1 Infection—Results of a 48-Week Controlled Study, (2007) J Acquir Immune Defic Syndr, 46(2):125-133.

Mascolini and Kort, 5th International AIDS Society Conference on HIV Pathogenesis, Treatment and Prevention: summary of key research and implications for policy and practice—Clinical sciences, 5th IAS Conference on HIV Pathogenesis, Treatment and Prevention (IAS 2009) Cape Town, South Africa, Jul. 19-22, 2009, J Int'l AIDS Society 2010, 13(Suppl 1):S3.

The Merck Index, An Encyclopedia of Chemicals, Drugs, and Biologicals, Fourteenth Edition 2006.

Min, et al., Pharmacokinetics and Safety of S/GSK1349572, a Next-Generation HIV Integrase Inhibitor, in Healthy Volunteers, Antimicrobial Agents and Chemotherapy, (Jan. 2010) 54(1):254-258 (published online ahead of print Nov. 2, 2009).

Min, et al., Pharmacokinetics (PK) and Safety in Healthy Subjects of S/GSK1349572, a Next-Generation, Once-Daily HIV Integrase Inhibitor (INI), 5th IAS Conference on HIV Pathogenesis, Treatment and Prevention, Jul. 19-22, 2009, Capetown, South Africa.

Musime, et al., Pharmacokinetics and acceptability of once- versus twice-daily lamivudine and abacavir in HIV type-1-infected Ugandan children in the Arrow Trial, (2010) Antiviral Therapy 15:1115-1124.

Powderly, et al., William G., Integrase inhibitors in the treatmetn of HIV-1 infection, Journal of Antimicrobial Chemotherapy, Journal of Antimicrobial Chemotherapy Advance Access publlished Sep. 23, 2010. Downloaded Dec. 31, 2015 from http://jac.oxfordjournals.org/.

Prada and Markowitz, Novel integrase inhibitors for HIV, Expert Opin. Investig. Drugs (2010) 19(9):1087-1098.

Rockstroh, et al., Once-daily S/GSK1349572 combination therapy in antiretroviral-naïve adults: rapid and potent 24-week antiviral responses in Spring-1 (ING112276), Journal of the International AIDS Society 2010, 13(Suppl 4): O50.

Rockstroh, et al., Integrase Inhibitors: Why Do We Need a New Drug Class for HIV Therapy?, Eur J Med Res (2009) 14 (Suppl 111): 1-3.

Sax, et al., Abacavir-Lamivudine versus Tenofovir-Emtricitabine for Initial HIV-1 Therapy, N Engl J Med (2009) 361(23):2230-2240.

Sax, et al., Co-formulated elvitegravir, cobicistat, emtricitabine, and tenofovir versus co-formulated efavirenz, emtricitabine, and tenofovir for initial treatment of HIV-1 infection: a randomised, double-blind, phase 3 trial, analysis of results after 48 weeks, Lancet (2012) 379:2439-2448.

Somboonwit, et al., Abacavir and lamivudine combination, Expert Opin Drug Metab Toxicol (2009) 5(12):1599-1606.

Songh1, et al., The Effect of Ritonavir-Boosted Protease Inhibitors on the HIV Integrase Inhibitor, S/GSK1349572, in Healthy Subjects, Conference Reports for NATAP, 49th ICAAC, San Francisco, CA, Sep. 12-15, 2009 Internet Sep. 15, 2009 (Sep. 15, 2009), XP002697436, URL:http://www.natap.org/2009/ICCAC/ICCAC_52.htm [retrieved on May 21, 2013].

Taiwo, et al., Novel Antiretroviral Combinations in Treatment-Experienced Patients with HIV Infection, Drugs (2010) 70(13)1629-1642.

Taiwo, et al., Unmet therapeutic needs in the new era of combination antiretroviral therapy for HIV-1, Journal of Antimicrobial Chemotherapy (2010) 65:1100-1107.

Tricot, et al., Safety and Efficacy of Raltegravir in HIV-Infected Transplant Patients Cotreated with Immunosuppressive Drugs, American Journal of Transplantation 9, 1946-1952 (2009).

Underwood, et al., IAS 2009—5th Conference on HIV Pathogenesis, Treatment and Prevention, Jul. 19-22, 2009, Cape Town, South Africa—Abstract.

WHO Model List of Essential Medicines, 16th Edition (updated), Mar. 2010, Reprint of the text of the WHO Medicines web site http://www.who.int/medicines/publications/essentialmedicines/en/index.htm.

Young, et al., A Pilot Study of Abacavir/Lamivudine and Raltegravir in Antiretroviral-Naïve HIV-1-Infected Patients: 48-Week Results of the Shield Trial, HIV Clin Trials, (2010) 11(5):260-269.

Young, et al., A Pilot Study of Abacavir/Lamivudine and Raltegravir in Antiretroviral-Naïve HIV-1 Infected Subjects: 48-Week Results, Conference Reports for NATAP, AIDS 2010, 18th International AIDS Conference (IAC), Jul. 18-23, 2010, Vienna, Austria.

Young, et al., A Pilot Study of Abacavir/Lamivudine (ABC/3TC) and Raltegravir (RAL) in Antiretroviral Naïve HIV-1 Infected Subjects, EACS—12th European AIDS Conference Nov. 11-14, 2009, Cologne, Germany.

XVIII International AIDS Conference, Jul. 18-23, 2010, Vienna, Austria, Abstract Book vol. 2, THLBB205, p. 287, www.aids2010.org.

Walmsley, et al., Dolutegravir plus Abacavir-Lamivudine for the Treatmet of HIV-1 Infection, New Engl J Med (2013) 369:1807-1818, DOI: 10.1056/NEJMoa1215541—GSK—No Use Without Permission.

International Search Report and Written Opinion for Priority Application No. PCT/US2011/22219.

European Search Report dated Aug. 14, 2015, for Co-related EP Application No. 15164931.6.

European Supplementary Search Report dated May 31, 2013, for Co-related EP Application No. 11737484.3.

Notice of Opposition by LaFrancol S.A. filed May 28, 2013, against Colombian Patent Application No. 12-125-933.

GlaxoSmithKline Response to Notice of Opposition by LaFrancol S.A. filed May 28, 2013, against Colombian Patent Application No. 12-125-933.

Notice of Opposition by Industrial Association of Pharmaceutical Laboratories filed Sep. 24, 2013, against Chilean Patent Application No. 2080-2012—in Spanish, No English Translation Available At This Time.

GSK Response to Notice of Opposition by Industrial Association of Pharmaceutical Laboratories filed Sep. 24, 2013, against Chilean Application No. 8020-2012—in Spanish, No English Translation Available At This Time.

Notice of Opposition dated by Jan. 26, 2016, by Teva Pharmaceutical Industries against Co-related EP Application No. 117374843, EP Publication No. 2531027.

Notice of Opposition dated Feb. 4, 2016, by Ter Meer Steinmeister & Partner Patentanwalte against Co-related EP Application No. 11737484.3, EP Publication No. 2531027.

Notice of Opposition dated Feb. 5, 2016, by LEK Pharmaceuticals against Co-related EP Application No. 11737484.3, EP Publication No. 2531027.

Notice of Opposition dated Feb. 5, 2016, Annex 1, by LEK Pharmaceuticals against Co-related EP Application No. 11737484.3, EP Publication No. 2531027.

Notice of Opposition dated Feb. 5, 2016, by Page White Farrer Limited against Co-related EP Application No. 11737484.3, EP Publication No. 2531027.

(56) References Cited

OTHER PUBLICATIONS

Notice of Publication of Eurasian Search Report with the Search Report—English Translations of both documents.
Stellbrink, Hans-Jurgen, Novel compounds for the treatment of HIV type 1 infection, Antiviral Chemistry and Chemotherapy (2009) 19:189-200, pp. 189-190.
Beale, et al., Combinations of Reverse Transcriptase, Protease, and Integrase Inhibitors Can Be Synergistic in Vitro Against Drug-Sensitive and RT Inhibitor-Resistant Molecular Clones of HIV-1; Antiviral Research,,Jun. 1, 2000,Elsevier BV, NL; vol. 46, No. 3, pp. 223-232.
Boffito et al., Perspectives on the Barrier to Resistance for Dolutegravir + Lamivudine, a Two-Drug Antiretroviral Therapy for HIV-1 Infection; AIDS Research and Human Retroviruses; vol. 36, No. 1, 2020, pp. 13-18.
Boucher et al., Antimicrobial Agents and Chemotherapy, vol. 37, No. 10, pp. 2231-2234, Oct. 1993.
Cahn et al., Dual therapy with lopinavir and ritonavir plus lamuvidine versus triple therapy with lopinavir and ritonavir plus two nucleoside reverse transcriptase inhibitors in antiretroviral-therapy-naive adults with HIV-1 infection: 48 week results of the randomised, open label, non-inferiority GARDEL trial.; Lancet Infect Dis 2014; 14, pp. 572-580.
Cahn, et al., Dolutegravir plus lamivudine versus dolutegravir plus tenofovir disoproxil fumarate and emtricitabine in antiretroviral-naive adults with HIV-1 infection (Gemini-1 and Gemini-2): week 48 results from two multicentre, double-blind, randomised, non-inferiority, phase 3 trials. The Lancet; Jan. 2019; vol. 393; pp. 143-155.
Chemical Abstracts Registry Database entry for GSK1349572.
Declaration Under 37 CFR 1.132 of Tomokasu Yoshinaga, filed Oct. 2, 2018 filed in U.S. Appl. No. 15/366,442.
VanRoey, et al., How developing world concerns need to be part of drug development plans: a case study of four emerging antiretrovirals. Drug Discovery Today, (2008), vol. 13, No. 13/14, p. p. 601-605,[Y] 1-15.
EP Search Report, Appl. No. 15164931.6-1453—dated Aug. 14, 2015.
Ford, et al., Lack of Pharmacokinetic Interaction between Rilpivirin and Integrase Inhibitors Dolutegravir and GSK1265744. Antimicrobial Agents and Chemotherapy; vol. 57, No. 11; pp. 5472-5477; 2013.
Galizzi, et al., International Journal of Antimicrobial Agents, 55 (2020) pp. 1-8 https://doi.org/10.1016/j.ijantimicag.2020.105893.
Garvey, E. P., et al. The Naphthyridinone GSK364735 Is a Novel, Potent Human Immunodeficiency Virus Type 1 Integrase Inhibitor and Antiretroviral. Antimicrobial Agents and Chemotherapy, v. 52, n. 3, p. 901-908, 2008.
Gillman et al., J. Antimicrob Chemother, 2019, 74; pp. 2365-2369 (2019).
Hogg, et al., "Initial Therapy for HIV: can less be more?", The Lancet Infectious Diseases. Jul. 2014. vol. 14, pp. 535-537.
Isentress (raltegravir) Tablets; patient information leaflet; publicado pelo FDA em Jul. 2009.
Janssen, et al., In Search of a Novel Anti-HIV Drug: Multidisciplinary Coordination in the Discovery of 4-[[4-[[4-[(1E)-2-Cyanoethenyl]-2,6-dimethylphenyl]amino]-2-pyrimidinyl]amino]benzonitrile (R278474, Rilpivirine). Journal of Medicinal Chemistry, (Mar. 1, 2005), vol. 48, No. 6, pp. 1901-1909,[Y] 1-15.
Lambert-Niclot et al., J Antimicrob Chemother, 2016: 71, pp. 1056-1062.

Laskey, et al., Quantitative evaluation of the antiretroviral efficacy of dolutegrvir, JCI Insight, 1(19), pp. 1-8, Nov. 17, 2016.
Management of HIV: A Swing Back to the Future, Minnesota medicine, Oct. 2009,[retrieved on Jan. 22, 2015], URL, http://www.minnesotamedicine.com/Past-Issues/Past-Issues-2009/October-2009/Clinical-Alozie-Oct2009.
Miller, et al., Journal of Infections Diseases, 2004; 189, pp. 837-846.
Pilot Study With Isentress (Raltegravir) and Epzicom (Abacavir/Lamivudine) in Treatment Naïve HIV-Infected Subjects (Shield), ClinicalTrials.gov, 2009, URL, http://clinicaltrials.gov/ct2/show/NCT00740064.
Sato, A, et al., "S/GSK1349572 is a potent next-generation HIV integrase inhibitor", HIV Medicine, Oct. 19, 2009, Blackwell Science, Oxford, GB; vol. 10; p. 92.
Turner et al., Multiple Effects of M184V Resistance Mutation in the REverse Transcriptase of Human Immunodeficiency Virus Type 1. Clinical and Diagnostic Laboratory Immunology, Nov. 2003, vol. 10, No. 6, pp. 979-981.
Van Wyk et al., Efficacy and Safety of Switching to Dolutegravir/Lamivudine Fixed-Dose 2-Drug Regimen vs Continuing a Tenofovir Alafenamide-Based 3- or 4-Drug Regimen for Maintenance of Virologic Suppression in Adults Living With Human Immunodeficiency Virus Type 1: Phase 3,Randomized, Noninferiority Tango Study, Clin Infect Dis, Jan. 6, 2020, pp. 1-10.
Written Opinion dated Mar. 6, 2011 for International Application No. PCT/US1122219.
Supporting Material: Cahn, et al., www.thelancet.com, Nov. 9, 2018, pp. 1-13, http://dx.doi.org/10.1016/S0140-6736(18)32462-0.
"Supporting Material: Van Wyk et al., Clin Infect Dis, Jan. 6, 2020, pp. 1-10, an 6;ciz1243. doi: 10.1093/cid/ciz1243".
Margot, et al., "In Vitro Human Immunodeficiency Virus Type 1 Resistance Selections with Combinations of Tenofiverand Emtricitabine or Abacavir and Lamivudine."Antimicrobial Agents and Chemotherapy; 2006; p. 4087 vol. 50(12).
Toshinaga, et al., "Barrier to Resistance of Dolutegravir in Two-Drug Combinations " Antimicrobial Agents and Chemotherapy; 2019; pp. 1-6; vol. 63(3).
U.S. Appl. No. 15/366,442, Non-Final Rejection, dated Jul. 13, 2017.
U.S. Appl. No. 15/366,442, Applicants response to non-final rejection, filed Jan. 12, 2018.
U.S. Appl. No. 15/366,442, Final Rejection, dated Mar. 14, 2018.
U.S. Appl. No. 15/366,442, Applicants response to final rejection and claims, filed Sep. 12, 2018.
U.S. Appl. No. 15/366,442, Applicants supplemental response and claims, filed Oct. 4, 2018.
U.S. Appl. No. 15/366,442, Notice of Allowance dated Dec. 13, 2018.
U.S. Appl. No. 15/366,442, Request for Continued Examination filed Mar. 5, 2019.
U.S. Appl. No. 15/366,442, Notice of Allowance dated Jul. 22, 2019.
Kumar et al., Lamivudine for the Treatment of HIV, Expert Opin Drug Metab Toxicol, Dec. 13, 2009, vol. 6, No. 1, pp. 105-114.
ClinicalTrials Identifier: NCT00951015, "A Dose Ranging Trial of GSK1349572 and 2 NRTI in HIV-1 Infected, Therapy Naive Subjects (ING112276)" update posted Jan. 16, 2018, URL: https://clinicaltrials.gov/ct2/show/results/NCT00951015?view=results.
Dovato Prescribing Information, Mar. 2021.
Singapore Application No. 10201707183T, Search Report, dated Jul. 18, 2021.
Singapore Application No. 10201707183T, Written Opinion, dated Jul. 18, 2021.

ANTIVIRAL THERAPY

CROSS-REFERENCE TO RELATED APPLICATIONS

This application is filed as a continuation application of U.S. Ser. No. 15/366,566, filed on Dec. 1, 2016, which is a continuation of U.S. Ser. No. 15/073,728 filed on Mar. 18, 2016, which is a continuation application of U.S. Ser. No. 14/710,952 filed on May 13, 2015 (now abandoned), which is a continuation application of U.S. Ser. No. 13/575,380 filed on Jul. 26, 2012 (now abandoned), which is a National Phase application of International Application No. PCT/US2011/022219, filed Jan. 24, 2011, which claims priority from U.S. Provisional Application Ser. No. 61/298,589 filed Jan. 27, 2010, and the entire contents of each of the foregoing applications are hereby incorporated by reference.

BACKGROUND OF THE INVENTION

The human immunodeficiency virus ("HIV") is the causative agent for acquired immunodeficiency syndrome ("AIDS"), a disease characterized by the destruction of the immune system, particularly of $CD4^+$ T-cells, with attendant susceptibility to opportunistic infections, and its precursor AIDS-related complex ("ARC"), a syndrome characterized by symptoms such as persistent generalized lymphadenopathy, fever and weight loss. HIV is a retrovirus; the conversion of its RNA to DNA is accomplished through the action of the enzyme reverse transcriptase. Compounds that inhibit the function of reverse transcriptase inhibit replication of HIV in infected cells. Such compounds are useful in the prevention or treatment of HIV infection in humans.

In addition to CD4, HIV requires a co-receptor for entry into target cells. The chemokine receptors function together with CD4 as co-receptors for HIV. The chemokine receptors CXCR4 and CCR5 have been identified as the main co-receptors for HIV-1. CCR5 acts as a major co-receptor for fusion and entry of macrophage-tropic HIV into host cells. These chemokine receptors are thought to play an essential role in the establishment and dissemination of an HIV infection. Therefore, CCR5 antagonists are thought to be useful as therapeutic agents active against HIV.

As in the case of several other retroviruses, HIV encodes the production of a protease which carries out post-translational cleavage of precursor polypeptides in a process necessary for the formation of infectious virions. These gene products include pol, which encodes the virion RNA-dependent DNA polymerase (reverse transcriptase), an endonuclease, HIV protease, and gag, which encodes the core-proteins of the virion.

One focus of anti-viral drug design has been to create compounds which inhibit the formation of infectious virions by interfering with the processing of viral polyprotein precursors. Processing of these precursor proteins requires the action of virus-encoded proteases which are essential for replication. The anti-viral potential of HIV protease inhibition has been demonstrated using peptidyl inhibitors.

A required step in HIV replication in human T-cells is the insertion by virally-encoded integrase of proviral DNA into the host cell genome. Integration is believed to be mediated by integrase in a process involving assembly of a stable nucleoprotein complex with viral DNA sequences, cleavage of two nucleotides from the 3' termini of the linear proviral DNA and covalent joining of the recessed 3' OH termini of the proviral DNA at a staggered cut made at the host target site. The repair synthesis of the resultant gap may be accomplished by cellular enzymes. Inhibitors of HIV integrase can be effective in treating AIDS and inhibiting viral replication.

Administration of combinations of therapeutic compounds in the treatment of HIV infection and related conditions can result in potentiated antiviral activity, reduced toxicity, delayed progression to resistance, and increased drug efficacy. Combinations administered in a single dosage unit can result in increased patient compliance as the pill burden is reduced and dosing schedules are simplified. However, not all compounds are suitable for administration in combinations. Factors that influence the feasibility of combinations include the chemical instability of the compounds, size of the dosage unit, potential for antagonistic or merely additive activities of the combined compounds, and difficulties in achieving a suitable formulation.

There is continued need to find therapeutic agents suitable for use in combination and feasible pharmaceutical compositions to treat HIV infection. Due to their high potency and pharmacokinetic profile, certain HIV integrase inhibitors are attractive as components in combination therapy.

SUMMARY OF THE INVENTION

Figure 1:
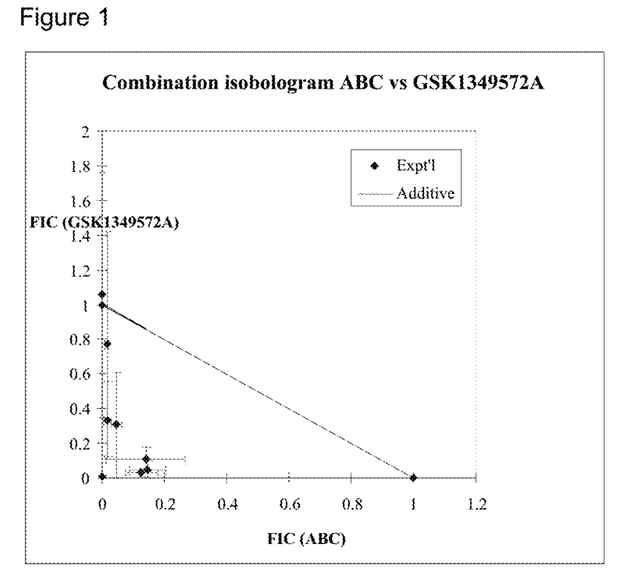
FIG. 1: Inhibition of HIV-1$_{IIIB}$ by a compound of formula (I), GSK1349572A, in combination with abacavir (ABC).
Figure 2:
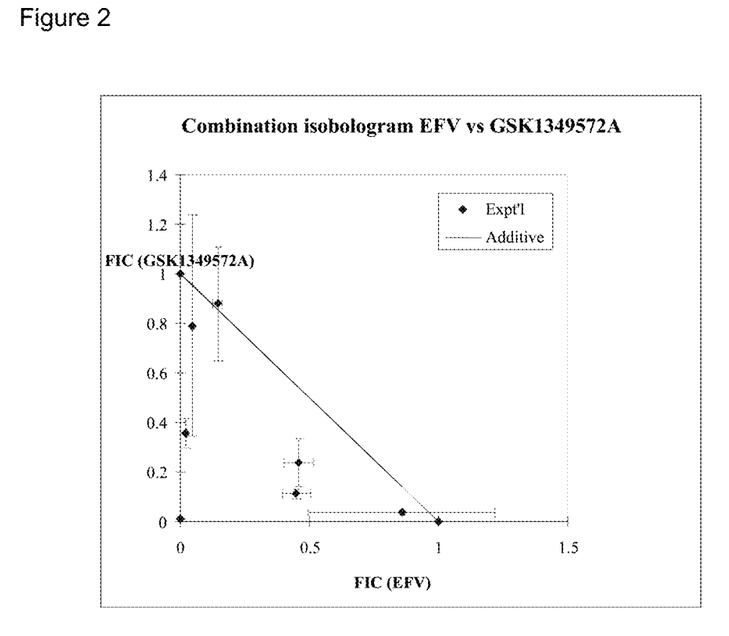
FIG. 2: Inhibition of HIV-1$_{IIIB}$ by a compound of formula (I), GSK1349572A, in combination with efavirenz (EFV).
Figure 3:
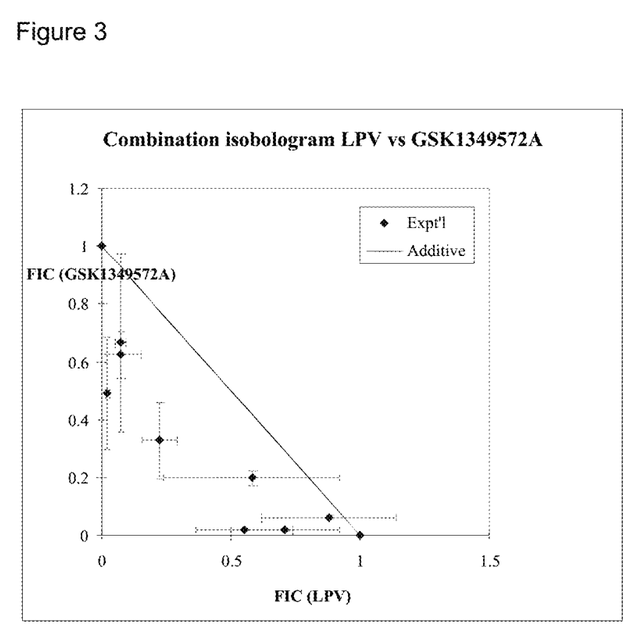
FIG. 3: Inhibition of HIV-1$_{IIIB}$ by a compound of formula (I), GSK1349572A, in combination with lopinavir (LPV)

The present invention relates to combinations of compounds comprising HIV integrase inhibitors and other therapeutic agents. Such combinations are useful in the inhibition of HIV replication, the prevention and/or treatment of infection by HIV, and in the treatment of AIDS and/or ARC. The present invention also features pharmaceutical compositions containing HIV integrase inhibitors.

DETAILED DESCRIPTION OF THE INVENTION

The present invention relates to combinations comprising a compound of the following formula (I), (II), or (III):

(I)

(II)

(III)

or a pharmaceutically acceptable salt thereof, and one or more therapeutic agents selected from the group consisting of nucleotide reverse transcriptase inhibitors, nucleoside reverse transcriptase inhibitors (NRTIs), non-nucleoside reverse transcriptase inhibitors (NNRTIs), protease inhibitors, CCR5 antagonists, CXCR4 antagonists, fusion inhibitors, maturation inhibitors, and integrase inhibitors.

The present invention relates to methods of treatment of HIV infection, AIDS, and AIDS related conditions by administering to a subject a compound of formula (I), (II), or (III) and one or more therapeutic agents selected from the group consisting of nucleotide reverse transcriptase inhibitors, nucleoside reverse transcriptase inhibitors (NRTIs), non-nucleoside reverse transcriptase inhibitors (NNRTIs), protease inhibitors, CCR5 antagonists, CXCR4 antagonists, fusion inhibitors, maturation inhibitors, and integrase inhibitors.

A compound of formula (I) is also known as GSK1349572. A chemical name of the compound of formula (I) is (4R, 12aS)—N-[2,4-flurophenyl)methyl]-3,4,6,8,12,12a-hexahydro-7-hydroxy-4-methyl-6,8-dioxo-2H-pyrido[1',2':4,5]pyrazino[2,1-b] [1,3] oxazine-9-carboxamide.

A chemical name of the compound of formula (II) is (3S, 11aR)—N-[(2,4-difluorophenyl)methyl]-2,3,5,7,11,11a-hexahydro-6-hydroxy-3-methyl-5,7-dioxo-oxazolo[3,2-a] pyrido [1,2-d] pyrazine-8-carboxamide.

A chemical name of the compound of formula (III) is (4aS,13aR)—N-[2,4-difluorophenyl)methyl]-10-hydroxy-9,11-dioxo-2,3,4a,5,9,11,13,13a-octahydro-1H-pyrido [1,2-a] pyrrolo[1',2':3,4,]imidazo[1,2-d]pyrazine-8-carboxamide.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the antiviral agent.

The term "treatment" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. Treatment may include prophylaxis which refers to preventing a disease or condition or preventing the occurrence of symptoms of such a disease or condition, in a patient. As used herein, the term "patient" refers to a mammal, including a human.

As used herein, the term "subject" refers to a patient, animal or a biological sample.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethane-sulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g. sodium), alkaline earth metal (e.g., magnesium), ammonium, $NW_4^+$ (wherein W is $C_{1-4}$ alkyl) and other amine salts. An advantageous salt is sodium salt.

Salts of the compounds of the present invention may be made by methods known to a person skilled in the art. For example, treatment of a compound of the present invention with an appropriate base or acid in an appropriate solvent can yield the corresponding salt.

The present invention relates to methods of treating or preventing viral infection, for example an HIV infection, in a human comprising administering to the human a therapeutically effective amount of a compound of formula (I), (II), or (III) or a pharmaceutically acceptable salt thereof in combination with one or more therapeutic agents selected from the group consisting of nucleotide reverse transcriptase inhibitors, nucleoside reverse transcriptase inhibitors (NRTIs), non-nucleoside reverse transcriptase inhibitors (NNRTIs), protease inhibitors, CCR5 antagonists, CXCR4 antagonists, fusion inhibitors, maturation inhibitors, and integrase inhibitors. The combination may be administered simultaneously or sequentially.

The compounds of formula (I), (II) and (III) are particularly suited to the treatment or prophylaxis of HIV infections and associated conditions. Reference herein to treatment may extend to prophylaxis as well as the treatment of established infections, symptoms, and associated clinical conditions such as AIDS related complex (ARC), Kaposi's sarcoma, and AIDS dementia.

Combination therapies comprise the administration of a compound of the present invention or a pharmaceutically acceptable salt thereof and another pharmaceutically active agent. The active ingredient(s) and pharmaceutically active agents may be administered simultaneously (i.e., concurrently) in either the same or different pharmaceutical compositions or sequentially in any order. The amounts of the active ingredient(s) and pharmaceutically active agent(s)

and the relative timings of administration will be selected in order to achieve the desired combined therapeutic effect.

Examples of such therapeutic agents include, but are not limited to, agents that are effective for the treatment of viral infections or associated conditions. Among these agents are nucleotide reverse transcriptase inhibitors, acyclic nucleoside phosphonates, for example (S)-1-(3-hydroxy-2-phosphonyl-methoxypropyl) cytosine (HPMPC), [[[2-(6-amino-9H-purin-9-yl)ethoxy] methyl]phosphinylidene] bis (oxymethylene)-2,2-dimethyl propanoic acid (bis-POM PMEA, adefovir dipivoxil), adefovir, [[(1R)-2-(6-amino-9H-purin-9-yl)-1-methylethoxy]methyl] phosphonic acid (tenofovir), tenofovir disoproxil fumarate, and (R)-[[2-(6-Amino-9H-purin-9-yl)-1-methylethoxy]methyl]phosphonic acid bis-(isopropoxycarbonyloxymethyl)ester (bis-POC-PMPA); nucleoside reverse transcriptase inhibitors, for example 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC, emtricitabine), (−)-cis-4-[2-amino-6-(cyclo-propylamino)-9H-purin-9-yl]-2-cyclopentene-1-methanol (abacavir), fozivudine tidoxil, alovudine, amdoxovir, elvucitabine, apricitabine, and festinavir (OBP-601); protease inhibitors, for example indinavir, ritonavir, nelfinavir, amprenavir, saquinavir, fosamprenavir, lopinavir, atazanavir, tipranavir, darunavir, brecanavir, palinavir, lasinavir, TMC-310911, DG-17, PPL-100, and SPI-256; non-nucleoside reverse transcriptase inhibitors (NNRTIs), for example nevirapine, delavirdine, efavirenz, GSK2248761 (IDX-12899), lersivirine (UK-453,061), rilpivirine (TMC-278), etravirine, loviride, immunocal, oltipraz, capravirine, and RDEA-806; integrase inhibitors, for example raltegravir, elvitegravir, and JTK-656; CCR5 and/or CXCR4 antagonists, for example, maraviroc, vicriviroc (Sch-D), TBR-652 (TAK-779), TAK-449, PRO-140, GSK706769, and SCH-532706; fusion inhibitors, for example enfuvirtide (T-20), T-1249, PRO-542, ibalizumab (TNX-355), BMS-378806 (BMS-806), BMS-488043, KD-247, 5-Helix inhibitors, and HIV attachment inhibitors; and maturation inhibitors, for example, bevirimat (PA-344 and PA-457).

The present invention features a combination comprising a compound of formula (I)

(I)

or a pharmaceutically acceptable salt thereof, and one or more therapeutic agents selected from the group consisting of lamivudine, abacavir, tenofovir, efavirenz, GSK2248761, lersivirine, lopinavir, fosamprenavir, and atazanavir.

The present invention also features a combination comprising a compound of formula (I) or a pharmaceutically acceptable salt thereof, and one or more therapeutic agents selected from abacavir, efavirenz, or lopinavir. The present invention features a combination comprising of a compound of formula (I) or a pharmaceutically acceptable salt thereof, and abacavir.

The present invention features a method of treatment of HIV infection comprising administering to a subject, a compound of formula (I), or a pharmaceutically acceptable salt thereof, and one or more therapeutic agents selected from the group consisting of lamivudine, abacavir, tenofovir, efavirenz, GSK2248761, lersivirine, lopinavir, fosamprenavir, and atazanavir.

The present invention features a method of treatment of HIV infection comprising administering to a subject, a compound of formula (I) or a pharmaceutically acceptable salt thereof, with one or more therapeutic agents selected from the group consisting of abacavir, efavirenz, and lopinavir. The present invention features a method of treatment of HIV infection comprising administering to a subject a compound of formula (I) or a pharmaceutically acceptable salt thereof, and abacavir.

The present invention features a pharmaceutical composition comprising a compound of formula (I) or a pharmaceutically acceptable salt thereof, and one or more therapeutic agents selected from the group consisting of: lamivudine, abacavir, efavirenz, tenofovir, GSK2248761, lersivirine, lopinavir, fosamprenavir, and atazanavir together with a pharmaceutically acceptable carrier therefor.

The present invention features a pharmaceutical composition comprising a compound of formula (I) or a pharmaceutically acceptable salt thereof, and one or more therapeutic agents selected from the group consisting of: abacavir, efavirenz, and lopinavir, together with a pharmaceutically acceptable carrier therefor. The present invention features a pharmaceutical composition comprising a compound of formula (I) or a pharmaceutically acceptable salt thereof, and abacavir together with a pharmaceutically acceptable carrier therefor.

The present invention features a combination comprising a compound of formula (II)

(II)

or a pharmaceutically acceptable salt thereof, and one or more therapeutic agents selected from the group consisting of lamivudine, abacavir, tenofovir, efavirenz, GSK2248761, lersivirine, lopinavir, fosamprenavir, and atazanavir The present invention also features a combination comprising a compound of formula (II) or a pharmaceutically acceptable salt thereof, and one or more therapeutic agents selected from abacavir, efavirenz, and lopinavir. The present invention features a combination comprising of a compound of formula (II) or a pharmaceutically acceptable salt thereof, and abacavir.

The present invention features a method of treatment of HIV infection comprising administering to a subject, a compound of formula (II) or a pharmaceutically acceptable salt thereof, and one or more therapeutic agents selected from the group consisting of lamivudine, abacavir, tenofovir, efavirenz, GSK2248761, lersivirine, lopinavir, fosamprenavir, and atazanavir.

The present invention features a method of treatment of HIV infection comprising administering to a subject, a compound of formula (II) or a pharmaceutically acceptable salt thereof, with one or more therapeutic agents selected from the group consisting of abacavir, efavirenz, and lopinavir. The present invention features a method of treatment of HIV infection comprising administering to a subject a compound of formula (II) or a pharmaceutically acceptable salt thereof, and abacavir.

The present invention features a pharmaceutical composition comprising a compound of formula (II) or a pharmaceutically acceptable salt thereof, and one or more therapeutic agents selected from the group consisting of: lamivudine, abacavir, tenofovir, efavirenz, GSK2248761, lersivirine, lopinavir, fosamprenavir, and atazanavir together with a pharmaceutically acceptable carrier therefor.

The present invention features a pharmaceutical composition comprising a compound of formula (II) or a pharmaceutically acceptable salt thereof, and one or more therapeutic agents selected from the group consisting of: abacavir, efavirenz, and lopinavir, together with a pharmaceutically acceptable carrier therefor. The present invention features a pharmaceutical composition comprising a compound of formula (II) or a pharmaceutically acceptable salt thereof, and abacavir together with a pharmaceutically acceptable carrier therefor.

The present invention features a combination comprising a compound of formula (III)

(III)

or a pharmaceutically acceptable salt thereof, and one or more therapeutic agents selected from the group consisting of lamivudine, abacavir, tenofovir, efavirenz, GSK2248761, lersivirine, lopinavir, fosamprenavir, and atazanavir The present invention also features a combination comprising a compound of formula (III) or a pharmaceutically acceptable salt thereof, and one or more therapeutic agents selected from abacavir, efavirenz, and lopinavir. The present invention also features a combination comprising a compound of formula (III) or a pharmaceutically acceptable salt thereof, and abacavir.

The present invention features a method of treatment of HIV infection comprising administering to a subject, a compound of formula (III) or a pharmaceutically acceptable salt thereof, and one or more therapeutic agents selected from the group consisting of lamivudine, abacavir, tenofovir, efavirenz, GSK2248761, lersivirine, lopinavir, fosamprenavir, and atazanavir.

The present invention features a method of treatment of HIV infection comprising administering to a subject, a combination of a compound of formula (III) or a pharmaceutically acceptable salt thereof, with one or more therapeutic agents selected from the group consisting of abacavir, efavirenz, and lopinavir. The present invention features a method of treatment of HIV infection comprising administering to a subject a compound of formula (III) or a pharmaceutically acceptable salt thereof, and abacavir.

The present invention features a pharmaceutical composition comprising a compound of formula (III) or a pharmaceutically acceptable salt thereof, and one or more therapeutic agents selected from the group consisting of: lamivudine, abacavir, tenofovir, efavirenz, GSK2248761, lersivirine, lopinavir, fosamprenavir, and atazanavir together with a pharmaceutically acceptable carrier therefor.

The present invention features a pharmaceutical composition comprising a compound of formula (III) or a pharmaceutically acceptable salt thereof, and one or more therapeutic agents selected from the group consisting of: abacavir, efavirenz, and lopinavir, together with a pharmaceutically acceptable carrier therefor. The present invention features a pharmaceutical composition comprising a compound of formula (III) or a pharmaceutically acceptable salt thereof, and abacavir together with a pharmaceutically acceptable carrier therefor.

The present invention features combinations, methods of treatment, and pharmaceutical compositions as described above wherein a pharmaceutically acceptable salt of a compound of formula (I), (II) or (III) is a sodium salt.

The present invention features combinations, methods of treatment, and pharmaceutical compositions as described above wherein one or more therapeutic agents are a pharmaceutically acceptable salt of said therapeutic agents, for example, abacavir hemisulfate, fosamprenavir calcium, atazanavir sulfate, tenofovir disoproxil sulfate, vicriviroc maleate or bevirimat dimeglumine.

The present invention features methods of treatment as described above wherein the subject is a human.

The present invention features combinations, methods of treatment and pharmaceutical compositions as described above wherein the combination is administered sequentially.

The present invention features combinations, methods of treatment and pharmaceutical compositions as described above wherein the combination is administered simultaneously or concurrently.

Compounds of formula (I), (II), and (III) may be made by methods disclosed in WO 2006/116764, U.S. 61/193,634 (WO2010/068253) or 61/193,636 (WO2010/068262), incorporated herein by reference hereto.

Abacavir may be made by methods disclosed in U.S. Pat. Nos. 5,034,394; 5,089,500; 6,294,540; 5,641,889; 5,840,990; 5,919,941; 5,808,147; 6,392,085; 6,448,403; 5,917,041; 6,087,501; 5,917,042; 6,555,687; 6,552,193; 6,870,053; 6,294,540; 6,340,587; or 6,646,125.

Lamivudine may be made by methods disclosed in U.S. Pat. Nos. 5,047,407; 7,119,202; 5,905,082; 5,696,254; 5,663,320; 5,693,787; 6,051,709; or 6,329,522.

Tenofovir may be made by U.S. Pat. Nos. 5,922,695; 5,935,946; 5,977,089; 6,043,230, 6,069,249.

Efavirenz may be made by may be made by methods disclosed in U.S. Pat. Nos. 5,519,021; 5,663,169; 5,811,423; 6,555,133; 6,639,071; or 6,939,964.

GSK2248761 may be made by methods disclosed in U.S. Pat. No. 7,534,809.

Lersivirine may be made by methods disclosed in U.S. Pat. No. 7,109,228.

Lopinavir may be made by methods disclosed in U.S. Pat. No. 5,914,332.

Fosamprenavir may be made by methods disclosed in U.S. Pat. Nos. 6,436,989; 6,514,953; or 6,281,367.

Atazanavir may be made by methods disclosed in U.S. Pat. No. 5,849,911 or 6,087,383.

The therapeutic agents of the combinations may be made according to published methods or by any method known to those skilled in the art.

In an aspect of the invention, a compound of formula (I), (II) or (III) or a pharmaceutically acceptable salt thereof may be formulated into compositions together with one or more therapeutic agents. The composition may be pharmaceutical composition, which comprises a compound of formula (I), (II), or (III), one or more therapeutic agents, and a pharmaceutically acceptable carrier, adjuvant or vehicle. In one embodiment, the composition comprises an amount of a combination of the present invention effective to treat or prevent viral infection, for example an HIV infection, in a biological sample or in a patient. In another embodiment, combinations of the invention and pharmaceutical compositions thereof, comprising an amount of a combination of the present invention effective to inhibit viral replication or to treat or prevent a viral infection or disease or disorder, for example an HIV infection, and a pharmaceutically acceptable carrier, adjuvant or vehicle, may be formulated for administration to a patient, for example, for oral administration.

The present invention features combinations according to the invention for use in medical therapy, for example for the treatment or prophylaxis of a viral infection, for example an HIV infection and associated conditions. The compounds according to the invention are especially useful for the treatment of AIDS and related clinical conditions such as AIDS related complex (ARC), progressive generalized lymphadenopathy (PGL), Kaposi's sarcoma, thromobocytopenic purpura, AIDS-related neurological conditions such as AIDS dementia complex, multiple sclerosis or tropical paraperesis, anti-HIV antibody-positive and HIV-positive conditions, including such conditions in asymptomatic patients.

According to another aspect, the present invention provides a method for the treatment or prevention of the symptoms or effects of a viral infection in an infected patient, for example, a mammal including a human, which comprises administering to said patient a pharmaceutically effective amount of a combination according to the invention. According to one aspect of the invention, the viral infection is a retroviral infection, in particular an HIV infection.

The present invention further includes the use of a combination according to the invention in the manufacture of a medicament for simultaneous (concurrent) or sequential administration to a subject for the treatment of a viral infection, in particular and HIV infection.

The present invention further provides a method for the treatment of a clinical condition in a patient, for example, a mammal including a human which clinical condition includes those which have been discussed hereinbefore, which comprises treating said patient with a pharmaceutically effective amount of a compound according to the invention. The present invention also includes a method for the treatment or prophylaxis of any of the aforementioned diseases or conditions.

Compounds of the present invention may be administered with an agent known to inhibit or reduce the metabolism of compounds, for example ritonavir. Accordingly, the present invention features a method for the treatment or prophylaxis of a disease as hereinbefore described by administration of a compound of the present invention in combination with a metabolic inhibitor. Such combination may be administered simultaneously or sequentially.

In general a suitable dose for each of the above-mentioned conditions will be in the range of 0.01 to 250 mg per kilogram body weight of the recipient (e.g. a human) per day, in the range of 0.1 to 100 mg per kilogram body weight per day; in the range 1 to 30 mg per kilogram body weight per day; in the range 0.5 to 20 mg per kilogram body weight per day. Unless otherwise indicated, all weights of active ingredients are calculated as the parent compound of formula (I), (II), or (III) and other therapeutic agents. For salts thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 1 to 2000 mg; 5 to 500 mg; 10 to 400 mg, 20 to 300 mg of each active ingredient per unit dosage form.

The combinations may be administered to achieve peak plasma concentrations of each active ingredient.

While it is possible for the active ingredients to be administered alone, it is preferable to present it as a pharmaceutical composition. The compositions of the present invention comprise an active ingredient, as defined above, together with one or more acceptable carriers thereof and one or more additional therapeutic agents. Each carrier must be acceptable in the sense of being compatible with the other ingredients of the composition and not injurious to the patient.

Pharmaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of the present invention or a pharmaceutically acceptable derivative thereof and another therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research* 3(6), 318 (1986).

Pharmaceutical compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions suitable for vaginal administration may be presented as pessaries, tampons, creams, gels, pastes, foams or spray. Pharmaceutical compositions may contain in addition to the active ingredient such carriers as are known in the art to be appropriate.

Pharmaceutical compositions for rectal administration may be presented as a suppository with a suitable carrier comprising, for example, cocoa butter or a salicylate or other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Unit dosage pharmaceutical compositions include those containing a daily dose or daily subdose of the active ingredients, as hereinbefore recited, or an appropriate fraction thereof.

Pharmaceutical compositions of the present invention may be presented as patient packs containing one or more courses of treatment in a single package, for example, a blister pack. It will be understood that the administration of the combination of the invention by means of a single patient pack, or patient packs of each composition, is an additional feature of the invention.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

EXAMPLES

Example 1: Biological Activity

Assays
Method

Antiviral HIV activity was measured by means of a tetrazolium-based colorimetric procedure in the human T-cell leukemia virus (HTLV-1) transformed cell line MT-4. Aliquots of test compound were diluted vertically across a deep-well master assay plate, in medium (RPMI 1640, 10% vol./vol. fetal bovine serum (FBS), and 10 µg/mL gentamicin), at concentrations that were approximately 40-fold higher than the final assay concentration. Serial dilutions were made at either 1:2 or 1:3.16 ratios. HIV inhibitors were diluted horizontally across master assay plates, also in concentrations that were approximately 40-fold higher than the final assay concentration. Small aliquots of both the vertically-diluted and the horizontally-diluted compounds were combined in daughter plates using an automated 96-well pipetting system (RapidPlate-96, Zymark Corp.). Checkerboard style dilutions were arranged so that every concentration of test compound was tested in the presence and absence of every concentration of the HIV inhibitors. Anti-HIV activity tests were performed in triplicate assays, or more, of each combination. Exponentially growing MT-4 cells were harvested and centrifuged at 1,000 rpm for 10 minutes in a Jouan centrifuge (Model CR 4 12). Cell pellets were re-suspended in fresh medium (RPMI 1640, 20% vol./vol. FBS, 20% vol./vol. IL-2, and 10 µg/mL gentamicin) to a density of $1.25 \times 10^6$ cells/mL. Cell aliquots were infected by the addition of HIV-1 (strain IIIB) diluted to give a viral multiplicity of infection (MOI) of 73 pfU per $1 \times 10^4$ cells. A similar cell aliquot was diluted with medium to provide a mock-infected control. Cell infection was allowed to proceed for 1 hour at 37° C. in a tissue culture incubator with humidified 5% $CO_2$ atmosphere. After the 1 hour incubation the virus/cell suspension was added to each well of the plates containing pre-diluted compounds. Plates were then placed in a tissue culture incubator with humidified 5% $CO_2$ for 5 days. At the end of the incubation period, 404 of CellTiter 96 MTS reagent (Promega no. G3581) was added to each well of the incubation plate. Plates were incubated at 37° C. for 2 to 3 hours to allow for color development.

O.D. was measured at 492 nM using a microplate absorbance reader (Tecan no. 20-300).

Virus Used

HIV-1 strain IIIB, wild-type laboratory strain, virus titer=6.896 E4 $TCID_{50}$/mL.

Data Analysis

Although some assay formats might theoretically miss antagonism due to combination cytotoxicity, the approach described here should not miss an antagonistic effect. The readout in the MT-4 cell assay utilizes MTS, a tetrazolium-based staining reagent where changes in optical density (O.D.) of the reagent are used to estimate the total cell number remaining after treatment. Final MT-4 cell numbers may decrease due to two effects. First, an HIV-induced cytotoxicity may occur when HIV kills greater than 75% of the MT-4 cells during the 5 days following infection. Second, a compound-induced cytotoxicity may occur, where the compound either directly kills the MT-4 cells or prevents cell growth (stasis) over the 5 days in either infected or uninfected cells. In either of these situations the O.D. is low as compared with infected cells protected by anti-HIV-1 compounds or relative to untreated and uninfected control cells. Since both cytotoxic effects and antagonism of anti-HIV activity would lead to lower O.D. we should not miss an antagonistic effect due to combination cytotoxicity, but could underestimate synergistic combinations.

Within assay combination cytotoxicity was evaluated by comparing wells containing the uninfected MT-4 cells from the assay plates that contained the highest concentration of test compound or the comparator compound, with wells containing HIV-1 infected MT-4 cells under the corresponding highest combination concentrations. For each of these values there is one well per assay plate and thus at least 3 wells per combination assay. Although they do not comprise a formal combination cytotoxicity analysis, the ratio of compound in combinations to compound alone provides a measure of the compound combination cytotoxicity within the concentrations examined.

The interaction of each pair of compound combinations was analyzed by the methods described by Selleseth, D. W. et al. (2003) Antimicrobial Agents and Chemotherapy 47:1468-71. Synergy and antagonism are defined as deviations from dosewise additivity, which results when two drugs interact as if they were the same drug. Values for average deviation from additivity in the range of −0.1 to −0.2 indicate weak synergy and values that approach −0.5 would indicate strong synergy of the interaction. Conversely, positive values of 0.1 to 0.2 would indicate that a weak antagonism exists between the treatments.

Results

A compound of formula (I) was found to be additive with raltegravir, adefovir, and maraviroc and was not affected by the presence of ribavirin. A compound of formula (I) was found to be synergistic with stavudine, abacavir, efavirenz, nevirapine, lopinavir, amprenavir, enfuvirtide.

What is claimed is:

1. A combination consisting essentially of a compound of formula (I)

or a pharmaceutically acceptable salt thereof, and lamivudine, or a pharmaceutically acceptable salt thereof.

2. A combination according to claim 1 wherein the pharmaceutically acceptable salt of the compound of formula (I) is a sodium salt.

3. A method of treatment of HIV infection consisting essentially of administering to a human in need thereof, a compound of formula (I)

or a pharmaceutically acceptable salt thereof, and lamivudine, or a pharmaceutically acceptable salt thereof.

4. The method according to claim 3, wherein the pharmaceutically acceptable salt of a compound of formula (I) is the sodium salt.

5. A pharmaceutical composition consisting essentially of a compound of formula (I)

or a pharmaceutically acceptable salt thereof, and lamivudine, or a pharmaceutically acceptable salt thereof.

6. The composition according to claim 5, wherein the pharmaceutically acceptable salt of a compound of formula (I) is a sodium salt.

7. The combination according to claim 1 wherein the combination is administered simultaneously.

8. The combination according to claim 1 wherein the combination is administered sequentially.

9. A method of treatment according to claim 3 wherein the compound of formula (I) or a pharmaceutically acceptable salt thereof, and lamivudine or a pharmaceutically acceptable salt thereof, are administered simultaneously.

10. A method of treatment according to claim 3 wherein the compound of formula (I) or a pharmaceutically acceptable salt thereof, and lamivudine or a pharmaceutically acceptable salt thereof, are administered sequentially.

11. A patient pack consisting essentially of the compound of formula (I) according to claim 1 or a pharmaceutically acceptable salt thereof, and lamivudine or a pharmaceutically acceptable salt thereof.

12. A combination consisting essentially of a sodium salt of a compound of formula (I)

and lamivudine.

13. A method of treatment of an HIV infection consisting essentially of administering to a human in need thereof, a sodium salt of a compound of formula (I)

and lamivudine.

14. A method of treatment according to claim 13 wherein the sodium salt of the compound of formula (I) and lamivudine are administered simultaneously.

15. A method of treatment according to claim 13 wherein the sodium salt of the compound of formula (I) and lamivudine are administered sequentially.

16. A pharmaceutical composition consisting essentially of a sodium salt of a compound of formula (I)

and lamivudine.

* * * * *